United States Patent
Schwartz

(12) 
(10) Patent No.: US 6,399,796 B2
(45) Date of Patent: Jun. 4, 2002

(54) ACTIVATION OF A DIELS-ALDER REACTION OF A STEROL 5,7-DIENE

(75) Inventor: Michael M. Schwartz, Naperville, IL (US)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/809,673

(22) Filed: Mar. 15, 2001

Related U.S. Application Data

(60) Provisional application No. 60/190,365, filed on Mar. 17, 2000.

(51) Int. Cl.[7] .................................................. C07J 79/00
(52) U.S. Cl. ....................................... 552/545; 552/540
(58) Field of Search .................................. 552/540, 545

(56) References Cited

U.S. PATENT DOCUMENTS

| | | |
|---|---|---|
| 4,384,153 A | 5/1983 | Dessau |
| 4,413,154 A | 11/1983 | Dessau |
| 4,503,195 A | 3/1985 | Bauld et al. |
| 4,552,928 A | 11/1985 | Bauld et al. |
| 5,208,152 A | 5/1993 | Hilvert et al. |
| 5,237,074 A | 8/1993 | Tani et al. |
| 5,391,777 A | 2/1995 | Tanabe et al. |
| 5,460,949 A | 10/1995 | Saunders et al. |

FOREIGN PATENT DOCUMENTS

| | | |
|---|---|---|
| WO | WO 93/21205 | 10/1993 |

OTHER PUBLICATIONS

Gorman, et al., "Iron (III) 2-ethylhexanoate as a novel, stereoselective hetero-Diels-Alder catalyst," *Chem. Commun.*, vol. 1, pp. 25–26 (1998).

Akiyama, et al., "Brønsted acid-catalyzed aza Diels-Alder reaction of Danishefsky's diene with aldimine generated in situ from aldehyde and amine in aqueous media," *Tetrahedron Letters*, vol. 40, pp. 7831–7834 (1999).

Barton, et al., "Biosynthesis of Terpenes and Steroids. Part IX. The Sterols of Some Mutant Yeasts and their Relationship to the Biosynthesis of Ergosterol," *J. Chem. Soc. Perkin Transactions 1*, No. 11, pp. 1326–1333 (1974).

Barton, et al., "Biosynthesis of Terpenes and Steroids. Patr V. The Synthesis of Ergosta-5,7,22,24(28)-tetraen-3β-ol, a Biosynthesis Precursor of Ergosterol," *J. Chem. Soc. (C)*, No. 10, pp. 1968–1974 (1971).

*Primary Examiner*—Barbara P. Badio
(74) *Attorney, Agent, or Firm*—Bryan Cave LLP

(57) ABSTRACT

An improved process and composition are disclosed for isolation of steroids containing a 5,7-diene functionality from a sterol mixture that comprises formation of a Diels-Alder reaction product of the ster-5,7-dienol in the presence of at least a catalytic amount of an ethylenically unsaturated $C_{12}$–$C_{24}$ fatty carboxylic acid.

24 Claims, No Drawings

ACTIVATION OF A DIELS-ALDER REACTION OF A STEROL 5,7-DIENE

This application claims benefit of U.S. provisional application No. 60/190,365, filed Mar. 17, 2000.

TECHNICAL FIELD

The invention relates to a method for the activation of a Diels-Alder reaction. More specifically, the invention relates to the activation of a Diels-Alder reaction in a sterol 5,7-diene.

BACKGROUND OF THE INVENTION

In certain processes for the commercial production of sterols, a Diels-Alder addition is useful as a protection step and also for purification. Diels-Alder addition has proven useful in the commercial production of 25-hydroxyvitamin $D_3$. With the present state of the art, the economics of commercial 25-hydroxyvitamin $D_3$ production is strongly affected by the yield of the Diels-Alder reaction. It is therefore desirable to maximize the yield of the Diels-Alder reaction in commercial sterol production.

Diels-Alder reactions are the well-known chemical addition of a dienophile to a diene. Textbook methods to activate Diels-Alder reactions use electron-releasing groups to enhance the electron density of the pi-donor diene. Similarly, electron-withdrawing groups are used to decrease the electron density of the pi-acceptor, thus enhancing its electrophilicity. In some processes, such as commercial sterol production, it is not possible or practical to provide functional groups to activate the electron donor for a Diels-Alder reaction. Means to enhance a Diels-Alder reaction in commercial sterol production is sought.

In the art, a semisynthetic commercial production of 25-hydroxyvitamin $D_3$ involves the saponification of 5,7,24-cholestatrienyl esters from fermentation of a double mutant yeast to form the free 5,7,24-cholestatrienol (also known as 7-dehydrocholesterol or provitamin $D_3$). The mutant yeast here contains the erg6 mutation in zymosterol-24-methyltransferase, and a mutation in the expression of ergosta-5,7,24(28)-trienol-22-dehydrogenase enzyme (erg5) as described in U.S. Pat. No. 5,460,949, whose disclosures are incorporated by reference.

Saponification procedures are common in the art, particularly where the hydrolysis of esters in organic matter is desired. Saponification reactions involve treatment with a strong base, typically with heating.

The saponification reaction product also includes squalene, fatty acids, including saturated and unsaturated fatty acids, and other sterols, which can include unconjugated dienols, and mono-unsaturated sterols. To separate the cholestatrienol and other sterols including lanosterol, 4,4,-dimethylzymosterol, 4-methylzymosterol, zymosterol, cholesta-7,24-diene-3β-ol from that mixture. The pH is typically adjusted to about 7–8 pH units, and the saponificate is extracted with heptane, and the heptane extract is washed with water. The washed heptane extract is concentrated, and mixed with ethyl acetate. This is called the "sterol extract".

In a Diels-Alder protection and/or purification step of the art, the sterol extract is reacted with a dienophile to form a Diels-Alder adduct of the 5,7-diene of the cholestatrienol, while leaving the unconjugated dienols and other sterols unreacted. The dienophile is typically phthalhydrazine generated in situ from the reaction of aqueous bleach (sodium hypochlorite) on phthalhydrazide. The Diels-Alder adduct is then chromatographically separated from the unreacted yeast sterol mixture, the cholestatrienol is regenerated, further purified and used to make 25-hydroxyvitamin $D_3$. This reaction sequence is illustrated in U.S. Pat. No. 5,391,777, whose disclosures are incorporated by reference.

U.S. Pat. No. 5,208,152 describes catalysts of Diels-Alder reactions where the substrates are cyclic conjugated dienes having a fugitive leaving group. Those dienes are unlike sterols.

U.S. Pat. No. 4,503,195 discloses the use of di- and tri-phenylated cation radical polymers as Diels-Alder catalysts, wherein the cation radical is a Group VA element (e.g. nitrogen, phosphorus or arsenic).

U.S. Pat. No. 4,413,154 and U.S. Pat. No. 4,384,153 disclose Diels-Alder reactions of 1,3-butadiene and 4-vinylcyclohexene over molecular sieves/zeolites.

BRIEF SUMMARY OF THE INVENTION

In accordance with the present invention, it has unexpectedly been found that the presence of at least a catalytic amount of an unsaturated $C_{12}$–$C_{24}$ fatty carboxylic acid enhances the formation of Diels-Alder adduct between a steroid 5,7-diene and a dienophile (preferably generated in situ from an oxidizable dienophile precursor and an oxidant). According to the invention, at least a catalytic amount of an unsaturated $C_{12}$–$C_{24}$ fatty carboxylic acid is exogenously provided to a Diels-Alder reaction.

The steroid 5,7-diene can be any such compound. Those that have been examined all undergo the Diels-Alder reaction with enhanced yield of adduct when at least a catalytic amount of a $C_{12}$–$C_{24}$ unsaturated carboxylic acid is added. Ergosterol and 5,7,24-cholestatrienol are preferred steroid 5,7-dienes, with 5,7,24-cholestatrienol being particularly preferred.

The present invention also contemplates an improved method of forming a Diels-Alder adduct with a 5,7-diene sterol comprising the following steps. A 5,7-diene sterol is admixed with a dienophile to form a reaction mixture, and thereby converting the 5,7-diene sterol to a Diels-Alder adduct. The 5,7-diene sterol has the structural formula

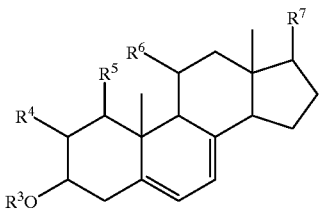

wherein $R^3$ is selected from the group consisting of H and $R^1CO$— wherein $R^1$ is monocyclic aryl of 5 to 7 carbon atoms or lower alkyl, and $R^4$, $R^5$ and $R^6$ are independently selected from the group consisting of H, hydroxyl, and lower alkyl, and $R^7$ is a $C_1$ to $C_{10}$ hydrocarbyl group. In one preferred embodiment, the 5,7-diene steroid compound is cholesta-5,7,24-triene-3-ol. Further chemical conversion of the Diels-Alder adduct to provide a modified Diels-Alder adduct is optionally conducted. The Diels-Alder adduct or the modified Diels-Alder adduct is separated from the mixture.

The invention contemplates adding at least a catalytic amount of an ethylenically unsaturated $C_{12}$ to $C_{24}$ fatty acid to the Diels-Alder reaction mixture. Preferably, the ethylenically unsaturated $C_{12}$ to $C_{24}$ fatty acid is linolenic acid, linoleic acid, oleic acid or a mixture of two or all three acids.

In one embodiment, the dienophile has the structural formula X—R=R—Y wherein the R groups are both N or both C-Q where the Q groups are H or together form a third bond, and wherein X and Y are selected from electron-withdrawing groups themselves independently selected from the group consisting of —COOH, —CHO, —NO$_2$, —CN, —COOR$^8$ and —COR$^8$, where R$^8$ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR$^2$ wherein R$^2$ is lower alkyl, H or monocyclic aryl of 5 to 7 carbon atoms and up to 5 ring substituents, wherein the ring substituents are selected from the group consisting of —(CH$_2$)$_n$—NH$_2$, —(CH$_2$)$_n$—COOH, —NO$_2$, halogen and lower alkyl, where n is an integer that is zero to 6, inclusive.

In another embodiment, the dienophile is generated in situ from (i) an oxidizable dienophile precursor and (ii) an oxidizing agent effective to oxidize the precursor to form the dienophile, wherein the dienophile precursor has the structural formula X—NH—NH—Y wherein X and Y are selected from electron-withdrawing groups themselves independently selected from the group consisting of —COOH, —CHO, —NO$_2$, —CN, —COOR$^8$ and —COR$^8$ where R$^8$ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR$^2$ wherein R$^2$ is lower alkyl, H or monocyclic aryl of 5 to 7 carbon atoms and up to 5 ring substituents, wherein the ring substituents are selected from the group consisting of lower alkyl, halogen, —NO$_2$, —(CH$_2$)$_n$—NH$_2$, and —(CH$_2$)$_n$—COOH, where n is an integer that is zero to 6, inclusive. Preferably, the oxidizable dienophile precursor is phthalhydrazine. Preferably, the oxidizing agent is hypochlorite (e.g. NaOCl or an aqueous solution of sodium hypochloride).

The present invention further contemplates a Diels-Alder reaction mixture initially comprising at least a catalytic amount of an exogenously added ethylenically unsaturated C$_{12}$ to C$_{24}$ fatty acid, a steroid 5,7-diene and a dienophile as discussed above.

The present invention has many benefits and advantages, several of which are listed below.

One benefit of the invention is that the Diels-Alder adduct is formed in enhanced yield.

An advantage of the invention is that the catalyst is quite inexpensive compared to the cost of the steroid co-reactant.

Another benefit of the invention is that the enhancement of Diels-Alder adduct formation leads to protection for a larger proportion of the 5,7-diene-containing sterol already present when the Diels-Alder addition is used for protection of the conjugated diene functionality.

Another advantage of the invention is that the enhancement of Diels-Alder adduct formation leads to more easy separation for a larger proportion of the 5,7-diene-containing sterol already present when the Diels-Alder reaction is used to assist in purification.

A further benefit of the invention is that neutralization of a saponification reaction with acid is not needed to carry endogenous unsaturated fatty acid forth in semisynthetic sterol production.

Still further benefits and advantages will be apparent to the worker of ordinary skill from the disclosure that follows.

DETAILED DESCRIPTION OF THE INVENTION

The present invention is, in part, an improvement on the method of U.S. Pat. No. 5,391,777, the disclosures of which are incorporated herein by reference. U.S. Pat. No. 5,391,777 describes the use of a Diels-Alder reaction to separate cholesta-5,7-diene-3β-25-diol and other steroid 5,7-dienes from a complex sterol solution. A 5,7-diene-containing steroid is reacted with a dienophile or an oxidizable dienophile precursor in combination with an oxidizing agent to provide a Diels-Alder adduct of the diene.

In the specification and the claims that follow, reference is made to a number of terms that are defined as follows.

"Exogenous" or "exogenously added" used herein in reference to a suitable unsaturated fatty acid that is separately added to the 5,7-diene-containing sterol, rather than already being with the sterol. For example, this does not refer to unsaturated fatty acid present in a sterol extract that came from the extracted cells.

"Alkyl" refers to a branched or unbranched saturated hydrocarbon group. Preferred alkyl groups herein contain 1 to 12 carbon atoms. "Lower alkyl" refers to an alkyl group of 1 to 6, more preferably 1 to 4, carbon atoms.

"Alkylene" refers to a molecular fragment that is a saturated branched or unbranched hydrocarbon chain, and includes, for example, ethylene (—CH$_2$—CH$_2$—). "Alkenylene" refers to a molecular fragment that is an unsaturated hydrocarbon chain, and includes, for example, ethenylene (—CH=CH—).

"Hydrocarbyl" refers to a branched or unbranched, saturated or unsaturated hydrocarbon group.

"Halo" or "halogen" refers to fluoro, chloro, bromo or iodo groups. Of the halos, chloro and bromo are generally preferred with chloro generally being the more preferred.

"Optional" or "optionally" means that the subsequently described event or circumstance may or may not occur, and that the description includes instances where the event or circumstance occurs and instances in which it does not. For example, "optionally substituted phenyl" means that the phenyl may or may not be substituted and that the description includes both unsubstituted phenyl and phenyl wherein there is substitution.

As used herein, the term "sterol" refers to unsaturated hydroxyl group-containing derivatives of a fused, reduced ring system, cyclopenta[a]-phenanthrene, comprising three fused cyclohexane rings (A, B and C) in a phenanthrene arrangement, and a terminal cyclopentane ring (D). The exemplary steroid below illustrates the numbering system employed herein in describing the location of groups and substituents.

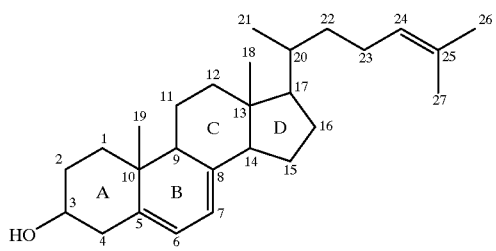

Several 5,7-diene containing sterols are candidates for application of the enhanced Diels-Alder reaction of the invention. These include analogs to natural sterols and novel synthetic 5,7-diene containing sterols in addition to natural 5,7-diene-containing sterols. There are several known natural 5,7-diene-containing sterols.

In nature, sterols are derived from acetate in complex biosynthetic cycles that share paths through the production of squalene. Acetyl coenzyme A (CoA) reacts with acetoacetyl CoA to form 3-hydroxy-3-methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through sequential steps of isomerization, condensation and dehydrogenation, IPP is converted to geranyl pyrophosphate (GPP). GPP combines with IPP to form farnesyl pyrophosphate (FP), two molecules of which are reductively condensed to form squalene, a 30-carbon precursor of sterols.

U.S. Pat. No. 5,460,949 describes a method for increasing the accumulation of squalene and specific sterols in yeast that comprises increasing the expression level of a structural gene encoding a polypeptide having HMG-CoA reductase activity in a mutant yeast having particular single or double defects in the expression of sterol biosynthetic enzymes.

The accumulation of squalene tends to enhance the production of sterols. In yeast, squalene is converted to squalene epoxide, which is then cyclized to form lanosterol. Lanosterol has two methyl groups at position 4, a methyl group at position 14, a double bond at position 8(9) and an 8 carbon side chain of the formula $CH_3CH(CH_2)_2CH=C(CH_3)_2$ bonded to the carbon at position 17. Lanosterol is sequentially demethylated at positions 14 and 4 to form zymosterol (cholesta-8,24-dienol), which is methylated on the side chain at position 17, and ultimately converted to ergosterol (ergosta-5,7,22-trienol), the most abundant sterol of naturally occurring, wild-type yeast. In the double mutant erg5-erg6 yeast utilized illustratively here in Example 1, the 17-position side chain is not methylated because of the erg6 mutation. In addition, the erg5 mutation stops dehydration at C-22 so that the cholesterol-type unsaturation in the C-17 side chain does not occur.

In animals such as mammals, including humans, lanosterol is also an intermediate in the synthesis of 5,7-diene-containing sterols. In one pathway, lanosterol is converted to 24,25-dihydrolanosterol, and then to 4α-methyl-Δ$^8$-cholesterol, 4α-methyl-Δ$^7$-cholesterol, Δ$^7$-cholesterol, 7-dehydrocholesterol (a 5,7-diene) and then to cholesterol. The position 17 side chain is not further alkylated in usual sterol syntheses in animals. Principles of Biochemistry, 6$^{th}$ Ed., Abraham White et al., eds., McGraw-Hill Book Company (New York: 1978), p. 619–630.

In higher plants such as tobacco, cotton, soybean, tomato and alfalfa, the side chain at position 17 is methylated in the formation of obtusifoliol, followed some steps later by a further methylation on that added carbon atom to ultimately form the intermediate Δ$^7$-avenasterol, which is a branch point in the synthesis. In one pathway, stigmasta-5,7,24(28)-trien-3β-ol is formed that leads to stigmasta-5,7-dien-3β-ol and then sitosterol or stigmasterol. In another pathway, Δ$^7$-avenasterol forms stigmasta-7-en-3β-ol, 7-dehydrostigmasterol (a 5,7-diene) and then stigmasterol. See, for example, U.S. Pat. No. 5,589,619, and the citations therein.

The 5,7-diene-containing sterols that are subjected to a Diels-Alder reaction in a process of the invention and that can be isolated and purified according to another process of the invention have the general structural formula:

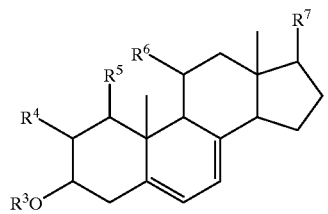

wherein $R^3$ is H or $R^1CO$— where $R^1$ is lower alkyl or monocyclic aryl of 5 to 7 carbon atoms, and $R^4$, $R^5$ and $R^6$ are independently selected from the group consisting of H, hydroxyl and lower alkyl. The $R^3$ moiety, if other than H, is often considered a hydroxyl-protecting group. Typical $R^3$ moieties are H, $CH_3CO$— and $C_6H_5CO$—. If $R^4$, $R^5$ and $R^6$ are other than H or OH, they are preferably methyl or ethyl, more typically methyl. $R^7$ is a 1 to 10 carbon atom hydrocarbyl group that can be straight or branched and saturated or unsaturated.

Structural formulas of preferred 5,7-diene sterols are shown below, and include 7-dehydroepisterol, 7-dehydroavenasterol, ergosterol, ergosta-5,7,22,24-tetraenol, stigmasta-5,7,24(28)-trien-3β-ol, stigmasta-5,7-dien-3β-ol, 7-dehydrositosterol, cholesta-5,7,24-trien-3β-ol and 7-dehydrocholesterol.

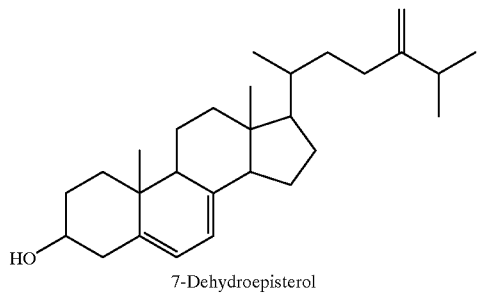

7-Dehydroepisterol

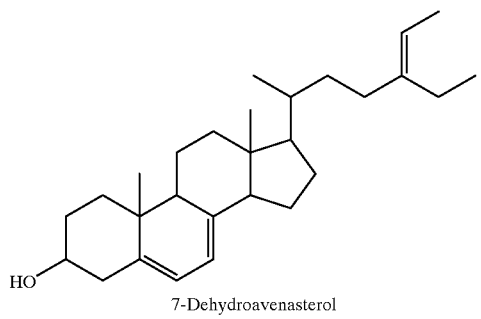

7-Dehydroavenasterol

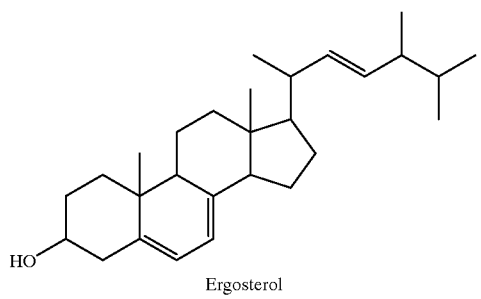

Ergosterol

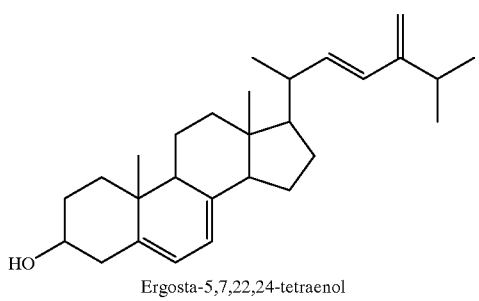

Ergosta-5,7,22,24-tetraenol

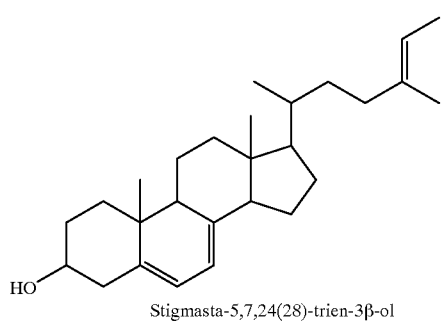

Stigmasta-5,7,24(28)-trien-3β-ol

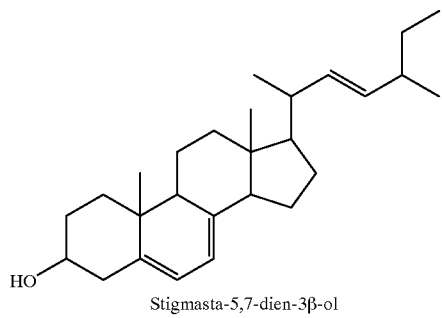

Stigmasta-5,7-dien-3β-ol

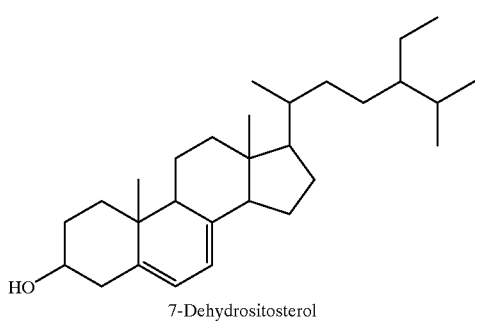

7-Dehydrositosterol

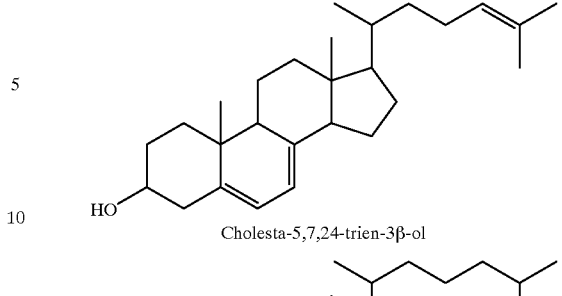

Cholesta-5,7,24-trien-3β-ol

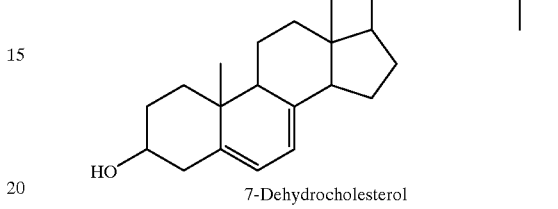

7-Dehydrocholesterol

A method of the present invention is particularly useful for isolating and purifying cholesta-5,7,24-triene-3β-ol from a mixture of sterols, as can be obtained from mutant yeast. A mixture of sterols in a mutant yeast extract typically contains the yeast metabolites squalene, lanosterol, 4,4-dimethylzymosterol, and the like in addition to triene. Other dienes present, e.g. other sterols having 5,7-dienes, in the yeast extract solution may also react with the dienophile.

It is also contemplated that other sterol compounds present in the composition from which a particular 5,7-diene-containing sterol is to be isolated contain two or more positions of ethylenic unsaturation, for example in the 8 to 10 carbon atom side chain $R^7$ as well as in the A or B steroid ring. Those diene compounds typically contain ethylenic unsaturation that is unconjugated, whereas the 5,7-double bonds are conjugated in the contemplated 5,7-diene-containing sterols. A contemplated 5,7-diene-containing sterol can also be said to have α,β-ethylenic unsaturation.

In one embodiment of the invention, the mixture of sterols is reacted in the presence of at least a catalytic amount of an exogenously added an unsaturated $C_{12}$–$C_{24}$ carboxylic acid with a dienophile having the structural formula X—R=R—Y, wherein the R groups are both N or both C-Q, where the Q groups are H or together form a third bond. Thus, the dienophile in this embodiment has the structure X—N=N—Y, X—(CQ)=(CQ)—Y, or X—C=C—Y. The substituents X and Y are electron-withdrawing groups that are independently selected from the group consisting of —COOH, —CHO, —NO$_2$, —CN, —COOR$^8$ and —COR$^8$, where R$^8$ is lower alkyl, or X and Y can be linked together to form a —(CO)—Z—(CO)— bridge. In the latter case; i.e., when X and Y are linked together, the "Z" linkage is lower alkylene, lower alkenylene, monocyclic arylene of 5 to 7 carbon atoms with up to 4 ring substituents, —S—, or —NR$^2$— wherein R$^2$ is lower alkyl, H or monocyclic aryl of 5 to 7 carbon atoms with up to 5 ring substituents. Ring substituents are selected from the group consisting of —(CH$_2$)$_n$—NH$_2$, —(CH$_2$)$_n$—COOH, —NO$_2$, halogen and lower alkyl, wherein n is an integer that is zero to 6, inclusive. This type of reaction of a dienophile with a 5,7-diene-containing sterol will sometimes be referred to herein as reaction type (1).

Dienophiles within the aforementioned group are available commercially or can be readily synthesized using starting materials and techniques known to those skilled in the art of synthetic organic chemistry. Examples of particular dienophiles useful herein include the following:

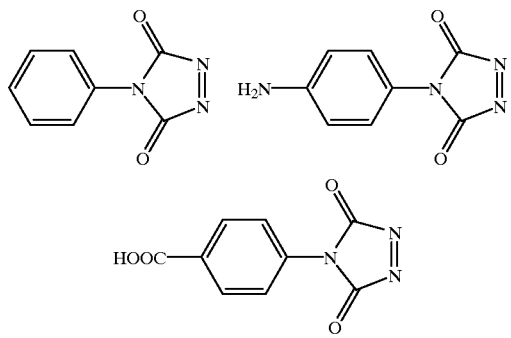

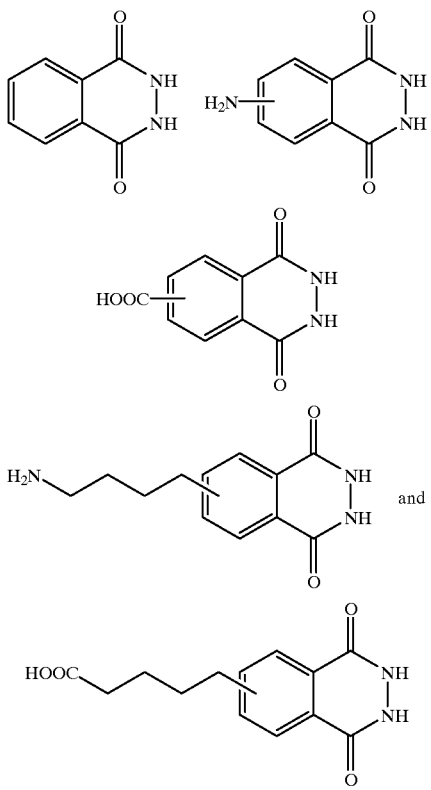

These dienophiles are available commercially from a number of sources, e.g., from the Aldrich Chemical Company, Milwaukee, Wis. As will be appreciated by those skilled in the art, such dienophiles may also be readily synthesized using conventional techniques. See, e.g., S. W. Moje and P. Beak, *J. Org. Chem.*, 39 (20):2951 (1974), and K. Rufenacht, *Helv. Chim. Acta*, 51:518 (1968).

In another embodiment, a dienophile precursor is used that is converted in situ into a dienophile with a suitable oxidizing agent. Here, the sterol mixture containing a 5,7-diene-containing sterol is simultaneously reacted in the presence of at least a catalytic amount of a $C_{12}$–$C_{24}$ carboxylic acid with the dienophile precursor and with an oxidizing agent effective to oxidize the precursor to an active dienophile. A reaction using a dienophile precursor described below and oxidant along with a mixture containing a 5,7-diene-containing sterol is sometimes referred to herein as reaction type (2).

The dienophile precursor has the structural formula X—NH—NH—Y wherein X and Y are electron-withdrawing groups that are independently selected from the group consisting of —COOH, —CHO, —NO$_2$, —CN, —COOR$^8$ and —COR$^8$ where R$^8$ is lower alkyl, or X and Y can be linked together to form a —(CO)—Z—(CO)— bridge. In the exemplary dienophile precursors wherein X and Y are linked together to form a —(CO)—Z—(CO)— bridge, the "Z" linkage is lower alkylene, lower alkenylene, monocyclic arylene of 5 to 7 carbon atoms with up to 4 ring substituents, —S—, or —NR$^2$—, wherein R$^2$ is H, lower alkyl or monocyclic aryl of 5 to 7 carbon atoms with up to 5 ring substituents. Ring substituents are selected from the group consisting of lower alkyl, halogen, —NO$_2$, —(CH$_2$)$_n$—NH$_2$, and —(CH$_2$)$_n$—COOH, wherein n is an integer that is zero to 6, inclusive.

Preferably, in this embodiment, Z is monocyclic arylene of 5 to 7 carbon atoms substituted with up to 2 substituents that are —(CH$_2$)$_n$—NH$_2$ or —(CH$_2$)$_n$—COOH, wherein n is an integer that is zero to 6, inclusive. Dienophile precursors within the aforementioned group are available commercially or can be readily synthesized using starting materials and techniques known to those skilled in the art of synthetic organic chemistry (see, e.g., H. D. K. Drew and H. H. Hatt, J. Chem. Soc. 16 (1937)). Examples of particular dienophile precursors useful herein (again, such compounds are available commercially, or can be readily synthesized) include the following:

In a contemplated 5,7diene-containing sterol production process of the invention, one or more unsaturated $C_{12}$–$C_{24}$ carboxylic acids such as linolenic acid, linoleic acid, and oleic acid are exogenously added to the Diels-Alder reaction solutions. Technical grade oleic acid is inexpensive and the impurities present in that commercially available grade, linoleic and linolenic acids, are also active ingredients in a reaction according to the invention. Technical grade oleic acid is a most preferred unsaturated $C_{12}$–$C_{24}$ carboxylic acid in a process of the invention.

The unsaturated acid is useful in trace quantities, for example about 0.02 weight percent of the reaction solution. However, its usefulness is not diminished by its presence in a larger quantity. Preferably, the lower amounts are used, about 0.05 to about 5 weight percent, most preferably about 0.1 to about 0.5 weight percent.

Unsaturated acids are present in sterol extracts from yeast fermentations in varying amounts. Typically, the variation is a result of the cellular extraction process. Such extraction often removes most of the unsaturated acids normally present in a cell lysate.

The addition of acid to bring down the pH of a caustic saponification/extraction solution can change the relative amounts of endogenous unsaturated acids that are soluble in the organic phase when protonated versus the ionized form of the endogenous unsaturated acids that are less soluble in the organic phase and more soluble in the aqueous phase of an extraction. The organic phase is the sterol extract. Not only the pH, but also the temperature of the water used to wash the organic phase, affects the amount of endogenous unsaturated acids that remain in the sterol extract. Thus, the amount of endogenous unsaturated acids present in a Diels-Alder reaction may be less than 0.02 weight percent, resulting in a low Diels-Alder adduct yield.

Lowering the pH of the saponification reaction before or during extraction is inadvisable from a practical standpoint for several reasons. The first is safety. The addition of a concentrated acid, such as sulfuric acid, to the caustic solution is an exothermic reaction that results in hot spots, and the splattering and splashing of the caustic and also may lead to structural problems with the reactor. A second reason is charring or the formation of black material in the solution. A third reason is gelling of the solution and soap formation. The latter two points lead to problems handling and successfully separating the 5,7-dienes from the solution. In sum, the best practice is not to add acid to the saponification reaction before or during extraction.

Saponification and extraction of the sterol from the yeast can be carried out using a very wide variety of solvents as may be appreciated by one with skill in the art. The current state of the art is to use hexane or heptane, preferably heptane for extracting the saponified 5,7-diene-containing sterol to make the sterol extract.

In a process according to the invention, the addition of exogenous unsaturated $C_{12}$–$C_{24}$ carboxylic acid provides the presence of a minimum amount of unsaturated acid in the Diels-Alder reaction solution. The enhancement of Diels-Alder reaction of the available 5,7-diene-containing sterols by the exogenously provided unsaturated acid thus helps to ensure that a high Diels-Alder adduct yield is obtained and that a low yield is not a result of the removal of "too much" endogenous unsaturated acid.

Exemplary unsaturated $C_{12}$–$C_{24}$ carboxylic acids useful herein are illustrated below. Use of a $C_{18}$ unsaturated fatty acid is preferred, with technical grade oleic acid being particularly preferred.

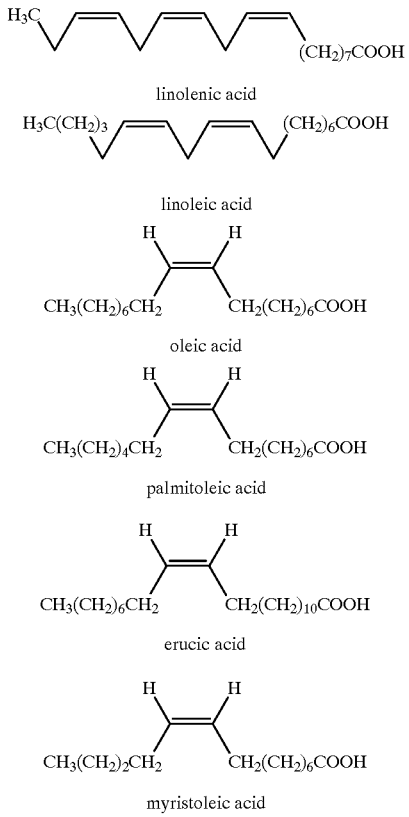

Exemplary compounds that are not within the scope of the phrase "unsaturated $C_{12}$–$C_{24}$ carboxylic acids" include oleyl alcohol, an unsaturated alcohol, and stearic acid, a $C_{18}$ saturated fatty acid, shown below.

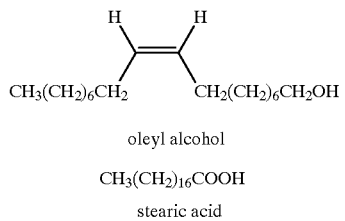

Any oxidizing agent capable of oxidizing the dienophile precursor to an active dienophile can be used, with the exception of oxidizing agents that interfere with the formation of the Diels-Alder adduct or that interact detrimentally in some other way with any of the sterols in the sterol mixture. Exemplary oxidizing agents include sodium hypochlorite, potassium peroxymonosulfate, lead tetraacetate, iodosobenzene diacetate, N-bromosuccinimide, and t-butyl hypochlorite. Preferably, aqueous sodium hypochlorite is used.

Either of the aforementioned reactions; i.e., reaction of the sterol mixture with a dienophile having the structure X—R═R—Y (Reaction 1), or with a dienophile formed in situ from a dienophile precursor of the structure X—NH—NH—Y and an oxidizing agent (Reaction 2), results in the formation of a Diels-Alder adduct. These reactions are illustrated in the following schemes:

Reaction 1

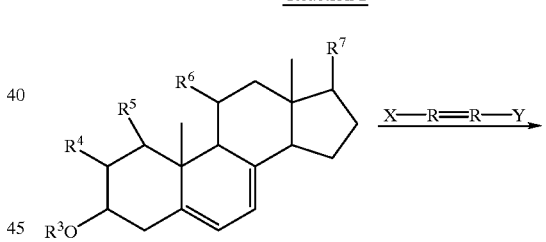

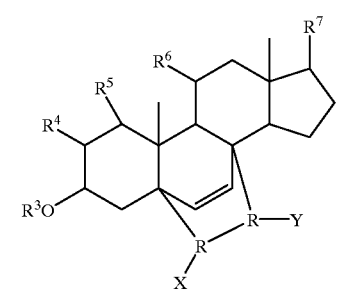

Reaction 2

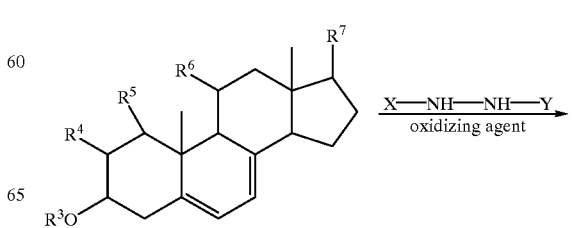

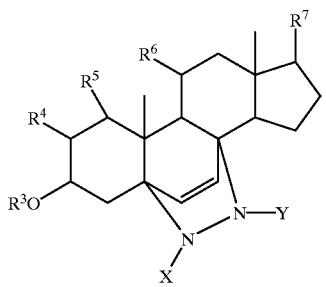

Both types of reactions are carried out in an inert atmosphere, in a non-reactive solvent. Polar organic solvents, for example ethyl acetate, methyl propionate and ethyl butyrate, are useful for keeping the sterols dissolved. Many polar organic solvents are known and selection is a matter of choice and there are several factors to consider. Halogenated solvents, such as chloromethane, could be used but are less preferred because of safety and handling considerations in an industrial setting. Lower boiling solvents are preferred for their ease in removal. Mixed solvent systems are also useful in a process of the invention. For example, in a contemplated semisynthetic process of making cholesta-5,7,24-trien-3-ol, the heptane used to make the sterol extract from the saponification reaction is not completely removed, so the reaction solution for the Diels-Alder addition step contains heptane in addition to the polar organic solvent.

With Reaction 2, it is preferred that the oxidizing agent be added gradually to a solution of the steroid and the dienophile precursor in the selected solvent. Reaction 2 is carried out at a temperature of zero degrees C to about 25° C., preferably at room temperature (about 20° C.). At least about 15 minutes, preferably at least 1 hour, should be allowed for Reaction 2 to occur.

After preparation of the Diels-Alder adduct using either Reaction 1 or Reaction 2, the adduct is removed from the reaction mixture and regenerated to provide the 5,7-diene-containing steroid in isolated form. Removal of the adduct from the reaction mixture is preferably done chromatographically, using, for example, a silica gel column that preferentially binds the Diels-Alder adduct.

The chemical and physical properties of the Diels-Alder adduct can be varied by manipulating the substituents present on the dienophile as well as by varying $R^3$. For example, basic properties can be imparted to the Diels-Alder adduct by the use of a dienophile containing a basic substituent, e.g., —$(CH_2)_n$—$NH_2$ where n is an integer that is zero to 6, inclusive, or the like. The adduct is then a basic molecule and separable from the sterol mixture using acid extraction. Similarly, acidic properties can be imparted to the Diels-Alder adduct by the use of a dienophile containing an acid substituent, e.g., —$(CH_2)_n$—COOH where n is an integer that is zero to 6, inclusive, or the like. The adduct is then an acidic molecule and separable from the sterol mixture using basic extraction.

Also, as alluded to above, after preparation of the Diels-Alder adduct, the moiety present at $R^3$ can be converted to a functionality that imparts desirable crystallization and/or precipitation properties. For example, a hydroxyl group present at position 3 can be readily converted to a benzoate species, which in turn can make the adduct more crystalline and more readily separable from the sterol mixture.

Regeneration of the 5,7-diene-containing steroid, e.g. from a protection or purification step utilizing Diels-Alder addition, is then accomplished by treatment of the adduct with a reducing agent such as lithium aluminum hydride ("LAH"), diisobutyl aluminum hydride ("DiBAL"), Red-Al® (a solution of sodium bis(2-methoxy-ethoxy)aluminum hydride in toluene, available from the Aldrich Chemical Company, Inc., Milwaukee, Wis.), or the like. Lithium aluminum hydride is particularly preferred. The reaction proceeds initially at a low temperature; i.e., 10° C. or lower (again, as can be obtained by an ice/water bath), followed by, after at least about 30 minutes, warming to at least about 50° C. for at least several minutes. Excess reducing agent and any salts or derivatives thereof are then removed, e.g., by hydrolysis plus filtration through Celite™ or the like. Evaporation of the reaction mixture provides the 5,7-diene-containing steroid.

Purification of the regenerated 5,7-diene-containing steroid can then be carried out using any of a number of techniques that are readily appreciated by those of ordinary skill in the art. For example, purification can be effected via recrystallization e.g., using methanol, ethanol, or the like, or using precipitation or chromatographic techniques.

As recited in U.S. Pat. No. 5,391,777, citing its parent, U.S. patent application Ser. No. 07/869,328, now abandoned, where the 5,7-diene-containing steroid is cholesta-5,7,24-triene-3β-ol, the isolated, purified material can be used to prepare cholesta-5,7-diene-3β,25-diol. Cholesta-5,7-diene-3β,25-diol is a biologically important hydroxylated pro-vitamin $D_3$ metabolite that can be converted by sunlight or other well-established photochemical methods to 25-hydroxy vitamin $D_3$. Such vitamin $D_3$ derivatives are useful in a number of contexts, e.g., in topical pharmaceutical formulations (for the treatment of skin disorders or the like), in oral vitamin compositions, and as livestock feed additives.

In a variation on the above-described reactions, chemical conversion of one or more sites on the 5,7-diene-containing steroid can be effected while the molecule is protected in the form of the Diels-Alder adduct. For example, the $\Delta^{24}$ double bond can be converted to a 24-amino-25-hydroxyl species, a 24,25-dihydroxyl species, or the like. Also, the "A" ring of the steroid can be oxidized when the compound is in adduct form. Examples of chemical conversions that can be carried out on the Diels-Alder adduct are described in patent application Ser. No. 07/869,328, noted previously.

EXAMPLE 1

Preparation of Yeast

Yeast strain ATC1562 is useful in preparing a composition that is high in cholesta-5,7,24-triene-3β-ol for use in a Diels-Alder reaction according to the invention. Yeast strain ATC1562 is derived from strain ATC1551. The construction of double mutant yeast strain ATC1551 is discussed in U.S. Pat. No. 5,460,949, the disclosures of which are incorporated herein by reference. Briefly, strain ATC0315rc (ATCC 74090, deposited Sep. 16, 1991) was transformed with plasmid pARC304S (ATCC 40916, Nov. 9, 1990) to create strain ATC1551, which resulted in a great degree of sterol accumulation, even with restricted aeration in the culture. ATC1551 (mata, erg5, erg6, TRP1+, URA3+) yeast was crossed with MC5 yeast (mate, ino-, ino-) to form yeast strain LS1003-1B (mata, erg5, erg6, TRP1+, URA3+). ATC1551 was separately crossed with yeast strain JGY230 (matα, his3-1, erg5) to form yeast strain LS1001-3B. Strain LS1003-1B and LS1001-3B were crossed to construct strain ATC1562 (mata/matα, erg5/erg5, erg6/erg6, TRP1+/TRP1+, URA3+/URA3−) or (matα/matα, erg5/erg5, TRP1/trp1, URA3/ura3) that is useful in preparing a yeast sterol extract that is high in cholesta-5,7,24-triene-3β-ol.

EXAMPLE 2

Diels-Alder Reactions in Cell-Derived Reaction Solutions

This Example demonstrates the range in variability in the yield of the Diels-Alder extract.

Sterol batches 6, 9, 10, 11 and 12 were from production saponification/extraction runs of fermentation of the double mutant strain ATC1562 described in Example 1.

Reactions were set up using an ethyl acetate/heptane solution of each sterol batch. Phthalhydrazide and hypochlorite were added to the stirred solutions such that the ratio of phthalhydrazide to sodium hypochlorite to 5,7-diene (cholestatrienol) was 4:2:1 to form the Diels-Alder reaction solutions.

Batches 6, 9, 11 and 12 all gave Diels-Alder adduct in about 90% yield. There was uncertainty about the yield of Diel-Alder adduct from Batch 10. The initial laboratory test of Batch 10 gave 100 percent yield. However, later tests using dip samples from stored drums of Batch 10 gave 25–41% yields of Diels-Alder adducts with incomplete conversion of cholestatrienol.

| Reaction | Initial Trienol Concentration (%) | Diels Alder Adduct Yield (%) |
|---|---|---|
| Batch 6; Run 267 | 3.95 | 91 |
| Batch 9; Run 268 | 3.43 | 88 |
| Batch 10; Run 271 | 2.60 | 100 |
| Batch 10 Dip Sample; Run 277 | 4.01 | 41* |
| Batch 10 Dip Sample; Run 278 | 4.01 | 25 |
| Batch 11; Run 270 | 4.30 | 89 |
| Batch 12; Run 269 | 4.11 | 89 |

*incomplete consumption of trienol

EXAMPLE 3

Model Reactions of Ergosterol Using Fractions of Yeast Sterol Extract

Studies with ergosterol as a model compound for the 5,7-diene in sterol extracts were conducted to isolate and identify the components in sterol extracts from erg5 and erg6 double mutant yeast fermentation for the large-scale production of Diels-Alder adduct of cholesta-5,7,24-trien-3-ol that enhanced Diels-Alder adduct formation.

The test procedure described in Example 2 was used in these studies. Instead of sterol extract, the standard feedstock for theses studies typically was 19 g of a 2 weight percent solution of ergosterol (Aldrich; 95%) in solvent consisting of about 50 weight percent ethyl acetate and 50 weight percent heptane.

The yield of Diels-Alder adduct with the above-mentioned ergosterol feedstock (control experiment) was less than 20 percent yield, and typically was less than 5 percent yield with incomplete conversion of ergosterol. The Diels-Alder adduct yield was zero percent with 46 percent unreacted ergosterol in Run 232.

A) The addition of total reaction product from Diels-Alder adduct formation with a typical sterol extract showed that component(s) were still present that promoted the reaction with ergosterol.

The Diels-Alder adduct yield was 68% when about 6 weight percent product solution from reaction G-8 (a typical run with sterol extract) was added to the feed in Run 196. The yield dropped to 28 percent with 30 percent un-reacted ergosterol when only 0.8 weight percent G-8 product solution was added to the feed in Run 197.

B) The addition of "wash solids" from the chromatographic purification of Diels-Alder adduct from a sterol extract showed that they contained the component(s) that promoted the reaction with ergosterol.

In these studies, silica gel chromatographic fractions of the sterol extract were added to model Diels Alder addition reactions using ergosterol.

The combined fractions of column effluent that eluted from the silica column before the Diels-Alder adduct fraction were concentrated on a rotary evaporator and the remaining material was added to model reactions with ergosterol at weight percents of 0.4, 0.7, 1.5, and 3. The ergosterol Diels-Alder adduct yield ranged from 60 to 68 percent in a non-linear manner.

Separate fractions of column effluent, again concentrated to remove the solvents, added at 3 weight percent to ergosterol model Diels-Alder addition reactions as described above resulted in Diels-Alder adduct yields ranging from zero to about 65% percent ergosterol Diels-Alder adduct, with the majority of the fractions having a yield of zero. In the reactions with a Diels-Alder adduct yield of zero, about 50–60% of the ergosterol was consumed. A few fractions had 62–65% ergosterol Diels-Alder adduct yield with consumption of 100% of the ergosterol. The few fractions that had 62–65% yield of ergosterol Diels-Alder adduct were very viscous and were made up primarily of fatty acids and other long chain compounds.

The conclusions of this study were that fatty acids or other long chain compounds are candidate components of some sterol extracts that permit enhanced Diels-Alder addition reaction yields. Diels-Alder adduct yield was insensitive to the amount of activating compound above a threshold of less than 0.4 weight percent.

EXAMPLE 4

Effect of Various Compounds on Model Reactions With Ergosterol

Several Diels-Alder activating candidate compounds were added to Diels-Alder model reactions with ergosterol. This Example demonstrates that unsaturated organic acids are Diels-Alder addition reaction activating compounds.

Model Diels-Alder addition reactions with ergosterol on 19 g scale with the oxidizable dienophile described hereinabove were carried out with a variety of exogenously provided compounds. The results of the study are as follows.

The reactions with added Triton® X-100 (Rohm & Haas; polyethylene glycol p-isooctylphenyl ether), stearic acid and oleyl alcohol essentially failed to activate the Diels-Alder reaction. There was moderate activation of the Diels-Alder reaction by Tween® 80 (polyoxyethylenesorbitan monooleate) and Tween® 20 (polyoxyethylenesorbitan monolaurate). Pure linolenic, linoleic, and oleic acids and technical grade oleic acid all gave Diels-Alder adduct with complete conversion of ergosterol. The data are provided below.

Run 229 without an additive but with a reaction temperature of 40–50° C. gave a 0.04% yield of Diels-Alder adduct with 19% un-reacted ergosterol.

Run 224 with 0.57 g Triton® X-100 (polyethylene glycol p-isooctylphenyl ether) gave a zero percent yield of Diels-Alder adduct with 50% unreacted ergosterol.

Run 250 with 0.57 g stearic acid gave a 16% yield of Diels-Alder adduct with zero percent unreacted ergosterol.

Run 257 with 0.58 g oleyl alcohol gave a zero percent yield of Diels-Alder adduct with 54% unreacted ergosterol.

Run 233 with 0.57 g Tween® 80 (polyoxyethylenesorbitan mono-oleate) gave a 49% yield of Diels-Alder adduct with zero percent unreacted ergosterol.

Run 234 with 0.57 g Tween® 20 (polyoxyethylenesorbitan mono-laurate) gave a 36% yield of Diels-Alder adduct with zero percent unreacted ergosterol.

Run 249 with 0.57 g of linoleic acid (Aldrich; 99%) gave a 62% yield of Diels-Alder adduct with zero percent un-reacted ergosterol.

Run 251 with 0.044 g of linoleic acid (Aldrich; 99%) gave a 59% yield of Diels-Alder adduct with zero percent un-reacted ergosterol. The linoleic acid was about 0.2 weight % of the total reaction charge. The molar ratio of linoleic acid to ergosterol was 0.16:1, indicating that the activation does not require the stoichiometric addition of unsaturated acid.

Run 252 with 0.034 g of linolenic acid (Aldrich; 99%) gave a 53% yield of Diels-Alder adduct with zero percent un-reacted ergosterol.

Run 254 with 0.376 g of oleic acid (Aldrich; 99%) gave a 63% yield of Diels-Alder adduct with zero percent un-reacted ergosterol.

Run 256 with 0.14 g of oleic acid (Aldrich; 99%) gave a 58% yield of Diels-Alder adduct with zero percent un-reacted ergosterol.

Run 255 with 0.14 g of technical-grade oleic acid (Aldrich; 90%) gave a 59% yield of Diels-Alder adduct with zero percent un-reacted ergosterol.

Run 273 with 0.14 g of technical oleic acid (Aldrich; 90%) with faster stirring than Run 255 gave a 65% yield of Diels-Alder adduct with zero percent un-reacted ergosterol. The stirrer setting in this and all subsequent runs was "4" unless otherwise indicated.

Run 274 with 0.14 g of technical oleic acid (Aldrich; 90%) with sonication instead of stirring gave a 46% yield of Diels-Alder adduct with zero percent un-reacted ergosterol. The phthalhydrazide starts as a fine suspension, but visibly clumps on the bottom of the flask during the bleach addition.

To summarize the conclusions from this Example, in the absence of an additive to activate the Diels-Alder reaction, there was essentially no Diels-Alder adduct formed from ergosterol with a reactive dienophile. The surfactant Triton® X-100 (Rohm & Haas; polyethylene glycol p-isooctylphenyl ether) also failed to activate the Diels-Alder reaction. The saturated stearic acid and the unsaturated alcohol oleyl alcohol also failed to activate the reaction. Linoleic, linolenic and oleic acid all enhanced the Diels-Alder reaction, including technical grade oleic acid.

There was a slight improvement in the activation with an unsaturated acid when the concentration of that saturated acid was increased from 0.2 weight percent to 2 weight percent, making it clear that non-stoichiometric amounts were required, more in line with catalytic amounts. Slight improvement was noted from faster stirring possibly resulting from enhanced contact with the unsaturated acid, however sonication depressed the activation relative to mechanical mixing.

It is noted that the best Diels-Alder adduct yields in the model reactions of 60–65% are still lower than the typical Diels-Alder adduct yield with ergosterol when oleic acid is present versus greater than 90% with cellular extract batches of sterols. However, these 60–65% yields agree with those obtained in Example 3, where yeast sterol extract fractions were used to activate the model reaction with ergosterol.

EXAMPLE 5

Effect of Varying Amounts of Oleic Acid on the Diels-Alder Reaction with Ergosterol Varying amounts of technical grade oleic acid (90% pure) were added to ethyl acetate (19 g; ACS Reagent Grade, 99.5% pure) solutions of ergosterol in a 50 mL Erlenmeyer flask fitted with a magnetic stirbar. Phthalhydrazide (2,3-dihydro-1,4-phthalazinedione; 170.17 g/mol; 99% pure phthalhydrazide from Aldrich, Milwaukee, Wis.) and sodium hypochlorite (74.44 g/mol in a 15–16% aqueous NaOCl solution) were added at ambient temperature in molar ratios of 4:2:1 phthalhydrazide to sodium hypochlorite to ergosterol.

| Weight Percent Technical Grade Oleic Acid | Ergosterol Diels-Alder Adduct Yield |
|---|---|
| 0.1 | 60% |
| 0.05 | 59% |
| 0.035 | 55% |
| 0.0275 | 56% |
| 0.020 | 0.03% |

This Example demonstrates that the minimum effective amount of unsaturated fatty acid required for substantial enhancement of the Diels Alder addition reaction is greater than 0.02 weight percent and less than 0.027 weight percent. At higher amounts of unsaturated fatty acid, the yield enhancement levels off, with no drop observed in this weight percent range.

EXAMPLE 6

Effect of Endogenous Fatty Acid on Diels-Alder Adduct Yield from Yeast

Example runs 204–223 were made using sterol batches obtained from yeast cell extract solids.

Run 210 and Run 214 with Batch 27 sterols each gave a 91% yield of Diels-Alder adduct. As-received Batch 27 had the following properties: 3.50% trienol; 31.9 mg/mL total fatty acid content.

Run 213 with Batch 28 sterols gave a 78% yield of Diels-Alder adduct. As-received Batch 28 had the following properties: 3.56% trienol; and 6 mg/ml total fatty acid content.

Run 219 with Batch 29 sterols gave a 75% yield of Diels-Alder adduct. As-received Batch 29 had the following properties: 3.85% trienol; and 4 mg/ml total fatty acid content.

Run 218 with Batch 1 sterols gave a 90% yield of Diels-Alder adduct. As-received Batch 1 had the following properties: 3.67% trienol and 80 mg/mL total fatty acid content.

Run 220 and Run 221 with Batch 2 sterols gave a 90% yield of Diels-Alder adduct. As-received Batch 2 had the following properties: 4.79% trienol and 8.6 mg/mL total fatty acid content.

Run 217 with Batch 3 sterols gave an 80% yield of Diels-Alder adduct. As-received Batch 3 had the following properties: 4.02% trienol and 5.0 mg/mL total fatty acid content.

Fatty acid content analyses of previously evaluated Batches 22–26 follow. Batch 22: 22.6 mg/mL. Batch 23: 0.5 mg/mL. Batch 24: 34.4 mg/mL. Batch 25: 0.9 mg/mL. Batch 26: and 22.3 mg/mL.

Fatty acid analyses were made according to methods known in the art of the batches or samples of the batches removed prior to the Diels-Alder reaction.

Diels-Alder adduct yield increased with increasing fatty acid content. A conservative interpretation of these results is that low fatty acid content is never necessary for high Diels-Alder adduct yield.

EXAMPLE 7

Direct Comparison of Diels-Alder Cholestatrienol Adduct Yields With and Without Added Oleic Acid The examples above reported the effect of the addition of exogenous unsaturated acid on the Diels-Alder adduct formation from ergosterol. In the present Example, the effect of exogenous unsaturated acid addition on the Diels-Alder adduct formation from cholesta-5,7,24-triene-3β-ol from yeast sterol extracts of the double mutant was monitored.

As was described in Example 2, Batch 10 dip samples gave Diels-Alder adduct yields of 25–41% with incomplete conversion of trienol when there was no exogenous unsaturated acid. The addition of technical grade oleic acid increased the Diels-Alder adduct yield to over 82% with complete conversion of the trienol.

Run 279 with 1 weight percent technical grade oleic acid added gave an 83% Diels-Alder adduct yield from Batch 10 Dip.

Run 282 with about 0.2 weight percent technical grade oleic acid gave an 82% Diels-Alder adduct yield from Batch 10 Dip.

Similarly, the as-received dip samples from Batches 3, 6, 7, 8, 9 and 11 from storage gave cholestatrienol Diels-Alder adducts of 21–56%, with incomplete converstion of cholestatrienol in Runs 286–296. The concentration of endogenous $C_{16}$ and $C_{18}$ unsaturated fatty acids in those as-received samples was 38–85 ppm (0.0038–0.0085 weight percent) in Batches 3, 6, 7, 8, 9 and 11.

The use of the above-mentioned Batch 7 dip sample with 0.2 wt. % exogenous technical grade oleic acid gave a 74% yield of Diels-Alder adduct in Run 297.

The use of the above-mentioned Batch 9 dip sample with 0.2 wt. % exogenous technical grade oleic acid gave a 68% yield of Diels-Alder adduct in Run 300.

The addition of oleic acid eliminates the sensitivity of Diels-Alder adduct formation to the unsaturated acid content in the sterol extract resulting from variation in the wash procedure. The exogenous addition eliminates the need to control for a specific unsaturated acid concentration during yeast cell solid extraction and washing. Direct addition of oleic acid eliminates the possibility of a low Diels-Alder adduct yield resulting from a variation in upstream handling that removed "too much" of the normally present unsaturated acids. For example, approximately 0.2 weight percent oleic acid addition is added to a typical run. Preferably, the minimum amount of oleic acid required is used to minimize any possible adverse effects on the subsequent wash and chromatography steps.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A Diels-Alder reaction method comprising the steps of:
   (a) admixing a 5,7-diene sterol, a dienophile and a catalytic amount of an exogenous ethylenically unsaturated $C_{12}$ to $C_{24}$ fatty carboxylic acid, wherein the 5,7,-diene sterol has the structural formula:

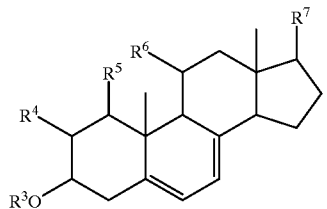

wherein $R^3$ is selected from the group consisting of H and $R^1CO$— wherein $R^1$ is monocyclic aryl of 5 to 7 carbon atoms or lower alkyl; $R^4$, $R^5$ and $R^6$ are independently selected from the group consisting of H, hydroxyl, and lower alkyl; and $R^7$ is a 1 to 10 carbon atom hydrocarbyl group;
   (b) maintaining the admixture for a time sufficient to permit the formation of a Diels-Alder adduct of the 5,7-diene sterol.

2. The method according to claim 1 wherein the ethylenically unsaturated $C_{12}$ to $C_{24}$ fatty acid is linolenic acid, linoleic acid, oleic acid or a mixture thereof.

3. The method according to claim 2 wherein the ethylenically unsaturated $C_{12}$ to $C_{24}$ fatty acid is oleic acid.

4. The method according to claim 1 wherein the 5,7-diene steroid compound is cholesta-5,7,24-triene-3-ol.

5. The method according to claim 1 wherein the dienophile has the structural formula X—R=R—Y wherein the R's are both N or both C-Q where the Q's are H or together form a third bond, and wherein X and Y are selected from electron-withdrawing groups themselves independently selected from the group consisting of —COOH, —CHO, —NO$_2$, —CN, —COOR$^8$ and —COR$^8$ where $R^8$ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR$^2$ wherein $R^2$ is H, monocyclic aryl of 5 to 7 carbon atoms or lower alkyl and up to 5 ring substituents, wherein the ring substituents are selected from the group consisting of —(CH$_2$)$_n$—, —NH$_2$, —COOH, —NO$_2$, halogen and lower alkyl, where n is an integer that is zero to 6, inclusive.

6. The method according to claim 1 wherein the dienophile is generated in situ from (i) an oxidizable dienophile precursor and (ii) an oxidizing agent effective to oxidize the precursor to form the dienophile, wherein the dienophile precursor has the structural formula X—NH—NH—Y wherein X and Y are selected from electron-withdrawing groups themselves independently selected from the group consisting of —COOH, —CHO, —NO$_2$, —CN, —COOR$^8$ and —COR$^8$ where $R^8$ is lower alkyl, or wherein X and Y are linked together to form a —(CO)—Z—(CO)— bridge in which Z is monocyclic arylene of 5 to 7 carbon atoms with up to 4 ring substituents, lower alkylene, or —NR² wherein R² is lower alkyl, H, or monocyclic aryl of 5 to 7 carbon atoms and up to 5 ring substituents, wherein the ring substituents are selected from the group consisting of —(CH$_2$)$_n$—NH$_2$, —(CH$_2$)$_n$—COOH, —NO$_2$, halogen and lower alkyl, where n is an integer that is zero to 6, inclusive.

7. The method according to claim 6 wherein the oxidizable dienophile is phthalhydrazide.

8. The method according claim 6 wherein the oxidizing agent is hypochlorite.

9. A Diels-Alder reaction mixture comprising:
(a) a 5,7,-diene sterol having the structural formula

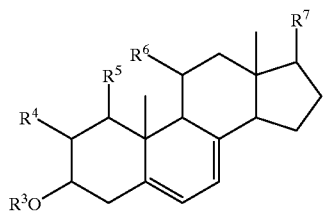

wherein R³ is selected from the group consisting of H and R¹CO— wherein R¹ is monocyclic aryl of 5 to 7 carbon atoms or lower alkyl; R⁴, R⁵ and R⁶ are independently selected from the group consisting of H, hydroxyl, and lower alkyl; and R⁷ is a 1 to 10 carbon atom hydrocarbyl group;
(b) a dienophile; and
(c) a catalytic amount of an exogenous ethylenically unsaturated C$_{12}$ to C$_{24}$ fatty carboxylic acid.

10. The mixture according to claim 9 wherein the ethylenically unsaturated C$_{12}$ to C$_{24}$ fatty acid is linolenic acid, linoleic acid, oleic acid or a mixture thereof.

11. The mixture according to claim 9 wherein the ethylenically unsaturated C$_{12}$ to C$_{24}$ fatty acid is oleic acid.

12. The mixture according to claim 9 wherein the 5,7-diene steroid compound is cholesta-5,7,24-triene-3-ol.

13. The mixture according to claim 9 wherein the dienophile has the structural formula X—R═R—Y wherein the R's are both N or both C-Q where the Q's are H or together form a third bond, and wherein X and Y are selected from electron-withdrawing groups themselves independently selected from the group consisting of —COOH, —CHO, —NO$_2$, —CN, —COOR⁸ and —COR⁸ where R⁸ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR² wherein R² is H, monocyclic aryl of 5 to 7 carbon atoms or lower alkyl and up to 5 ring substituents, wherein the ring substituents are selected from the group consisting of —(CH$_2$)$_n$, —NH$_2$, —COOH, —NO$_2$, halogen and lower alkyl, where n is an integer that is zero to 6, inclusive.

14. The mixture according to claim 9 wherein the dienophile is generated in situ from (i) an oxidizable dienophile precursor and (ii) an oxidizing agent effective to oxidize the precursor to form the dienophile, wherein the dienophile precursor has the structural formula X—NH—NH—Y wherein X and Y are selected from electron-withdrawing groups themselves independently selected from the group consisting of —COOH, —CHO, —NO$_2$, —CN, —COOR⁸ and —COR⁸ where R⁸ is lower alkyl, or wherein X and Y are linked together to form a —(CO)—Z—(CO)— bridge in which Z is monocyclic arylene of 5 to 7 carbon atoms with up to 4 ring substituents, lower alkylene, or —NR² wherein R² is lower alkyl, H, or monocyclic aryl of 5 to 7 carbon atoms and up to 5 ring substituents, wherein the ring substituents are selected from the group consisting of —(CH$_2$)$_n$—NH$_2$, —(CH$_2$)$_n$—COOH, —NO$_2$, halogen and lower alkyl, where n is an integer that is zero to 6, inclusive.

15. The mixture according to claim 14 wherein the oxidizable dienophile is phthalhydrazide.

16. The mixture according claim 14 wherein the oxidizing agent is hypochlorite.

17. In an improved method of isolating a 5,7-diene sterol from a mixture of sterols comprising the steps of:
(a) reacting a mixture of sterols that comprises a 5,7-diene sterol with a dienophile, to convert the 5,7-diene sterol to a Diels-Alder adduct,
wherein the 5,7-diene sterol has the structural formula

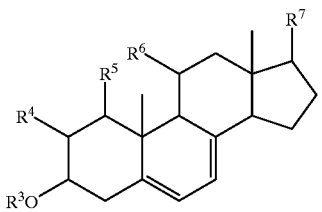

wherein R³ is selected from the group consisting of H and R¹CO— wherein R¹ is monocyclic aryl of 5 to 7 carbon atoms or lower alkyl; R⁴, R⁵ and R⁶ are independently selected from the group consisting of H, hydroxyl, and lower alkyl; and R⁷ is a 1 to 10 carbon atom hydrocarbyl group; and
(b) separating the Diels-Alder adduct or the modified Diels-Alder adduct from the mixture;
the improvement comprising adding to said mixture at least a catalytic amount of an ethylenically unsaturated C$_{12}$ to C$_{24}$ fatty carboxylic acid.

18. The method according to claim 17 wherein the ethylenically unsaturated C$_{12}$ to C$_{24}$ fatty acid is linolenic acid, linoleic acid, oleic acid or a mixture thereof.

19. The method according to claim 17 wherein the ethylenically unsaturated C$_{12}$ to C$_{24}$ fatty acid is oleic acid.

20. The method according to claim 17 wherein the 5,7-diene steroid compound is cholesta-5,7,24-triene-3-ol.

21. The method according to claim 17 wherein the dienophile has the structural formula X—R═R—Y wherein the R's are both N or both C-Q where the Q's are H or together form a third bond, and wherein X and Y are selected from electron-withdrawing groups themselves independently selected from the group consisting of —COOH, —CHO, —NO$_2$, —CN, —COOR⁸ and —COR⁸ where R⁸ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR² wherein R² is H, monocyclic aryl of 5 to 7 carbon atoms or lower alkyl and up to 5 ring substituents, wherein the ring substituents are selected from the group consisting of —(CH$_2$)$_n$, —NH$_2$, —COOH, —NO$_2$, halogen and lower alkyl, where n is an integer that is zero to 6, inclusive.

22. The method according to claim 17 wherein the dienophile is generated in situ from (i) an oxidizable dienophile precursor and (ii) an oxidizing agent effective to oxidize the precursor to form the dienophile, wherein the dienophile precursor has the structural formula X—NH—NH—Y wherein X and Y are selected from electron-withdrawing groups themselves independently selected from the group consisting of —COOH, —CHO, —NO$_2$, —CN, —COOR$^8$ and —COR$^8$ where R$^8$ is lower alkyl, or wherein X and Y are linked together to form a —(CO)—Z—(CO)— bridge in which Z is monocyclic arylene of 5 to 7 carbon atoms with up to 4 ring substituents, lower alkylene, or —NR$^2$ wherein R$^2$ is lower alkyl, H, or monocyclic aryl of 5 to 7 carbon atoms and up to 5 ring substituents, wherein the ring substituents are selected from the group consisting of —(CH$_2$)$_n$—NH$_2$, —(CH$_2$)$_n$—COOH, —NO$_2$, halogen and lower alkyl, where n is an integer that is zero to 6, inclusive.

23. The method according to claim 21 wherein the oxidizable dienophile is phthalhydrazide.

24. The method according claim 21 wherein the oxidizing agent is hypochlorite.

* * * * *